United States Patent
Lin et al.

(10) Patent No.: US 10,950,730 B2
(45) Date of Patent: Mar. 16, 2021

(54) MERGED SOURCE/DRAIN FEATURES

(71) Applicant: Taiwan Semiconductor Manufacturing Co., Ltd., Hsinchu (TW)

(72) Inventors: Chun-An Lin, Tainan (TW); Wei-Yuan Lu, Taipei (TW); Feng-Cheng Yang, Hsinchu County (TW); Tzu-Ching Lin, Hsinchu (TW); Li-Li Su, HsinChu County (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 27 days.

(21) Appl. No.: 16/529,357

(22) Filed: Aug. 1, 2019

(65) Prior Publication Data

US 2020/0135914 A1 Apr. 30, 2020

Related U.S. Application Data

(60) Provisional application No. 62/753,295, filed on Oct. 31, 2018.

(51) Int. Cl.
| | |
|---|---|
| *H01L 29/78* | (2006.01) |
| *H01L 29/66* | (2006.01) |
| *H01L 21/8238* | (2006.01) |
| *H01L 27/092* | (2006.01) |
| *H01L 21/02* | (2006.01) |
| *A61B 5/15* | (2006.01) |
| *G01N 1/14* | (2006.01) |

(Continued)

(52) U.S. Cl.
CPC ...... *H01L 29/785* (2013.01); *A61B 5/150099* (2013.01); *A61B 5/150992* (2013.01); *G01N 1/14* (2013.01); *G01N 33/4915* (2013.01); *H01L 21/02532* (2013.01); *H01L 21/823814* (2013.01); *H01L 21/823821* (2013.01); *H01L 21/823878* (2013.01); *H01L 27/0924* (2013.01); *H01L 29/66795* (2013.01); *H01L 29/045* (2013.01); *H01L 29/7853* (2013.01)

(58) Field of Classification Search
CPC ............ H01L 29/785; H01L 21/02532; H01L 21/623814; H01L 21/823821; H01L 21/823878; H01L 27/0924; H01L 29/66795
USPC ..................... 257/401, 396, 397; 438/298.45
See application file for complete search history.

(56) References Cited

U.S. PATENT DOCUMENTS

| | | |
|---|---|---|
| 8,836,016 B2 | 9/2014 | Wu et al. |
| 8,841,701 B2 | 9/2014 | Lin et al. |

(Continued)

*Primary Examiner* — Thinh T Nguyen
(74) *Attorney, Agent, or Firm* — Haynes and Boone, LLP

(57) ABSTRACT

The present application provides a semiconductor device and the method of making the same. The method includes recessing a fin extending from a substrate, forming a base epitaxial feature on the recessed fin, forming a bar-like epitaxial feature on the base epitaxial feature, and forming a conformal epitaxial feature on the bar-like epitaxial feature. The forming of the bar-like epitaxial feature includes in-situ doping the bar-like epitaxial feature with an n-type dopant at a first doping concentration. The forming of the conformal epitaxial feature includes in-situ doping the conformal epitaxial feature with a second doping concentration greater than the first doping concentration.

20 Claims, 8 Drawing Sheets

(51) Int. Cl.
  *G01N 33/49* (2006.01)
  *H01L 29/04* (2006.01)

(56) References Cited

U.S. PATENT DOCUMENTS

| | | |
|---|---|---|
| 8,847,293 B2 | 9/2014 | Lee et al. |
| 8,853,025 B2 | 10/2014 | Zhang et al. |
| 8,962,400 B2 | 2/2015 | Tsai et al. |
| 9,093,514 B2 | 7/2015 | Tsai et al. |
| 9,236,267 B2 | 1/2016 | De et al. |
| 9,245,805 B2 | 1/2016 | Yeh et al. |
| 9,520,482 B1 | 12/2016 | Chang et al. |
| 9,576,814 B2 | 2/2017 | Wu et al. |
| 2009/0267196 A1* | 10/2009 | Dyer et al. ........ H01L 29/66795 257/628 |

* cited by examiner

US 10,950,730 B2

MERGED SOURCE/DRAIN FEATURES

PRIORITY DATA

This application claims priority to U.S. Provisional Patent Application Ser. No. 62/753,295 entitled "Merged Source/Drain Features" and filed on Oct. 31, 2018, the entire disclosure of which is incorporated herein by reference.

BACKGROUND

The semiconductor integrated circuit (IC) industry has experienced rapid growth. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs. However, such scaling down has also been accompanied by increased complexity in design and manufacturing of devices incorporating these ICs. Parallel advances in manufacturing have allowed increasingly complex designs to be fabricated with precision and reliability.

For example, advances in fabrication have enabled three-dimensional designs, such as Fin-like Field Effect Transistors (FinFETs). An exemplary FinFET is fabricated with a thin "fin" (or fin-like structure) extending up from a substrate. Source/drain features may be formed in this vertical fin by recessing the fin material and epitaxially growing the source/drain features in its place. The remaining portions of the fin may form channel regions between the source/drain features, and a gate is provided over (e.g., wrapping around) the channel region of the fin. Wrapping the gate around the fin increases the contact area between the channel region and the gate and allows the gate to control the channel from multiple sides. This can be leveraged in a number of way, and in some applications, FinFETs provide reduced short channel effects, reduced leakage, and higher current flow. In other words, they may be faster, smaller, and more efficient than planar devices.

The scaling down of FinFETs introduces challenges to reduce parasitic capacitance between the source/drain feature and the gate and to lower resistance between the source/drain feature and the recessed fins. While conventional FinFET structures are generally adequate for their intended purposes, they are not satisfactory in all aspects.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

DETAILED DESCRIPTION

Figure 1:
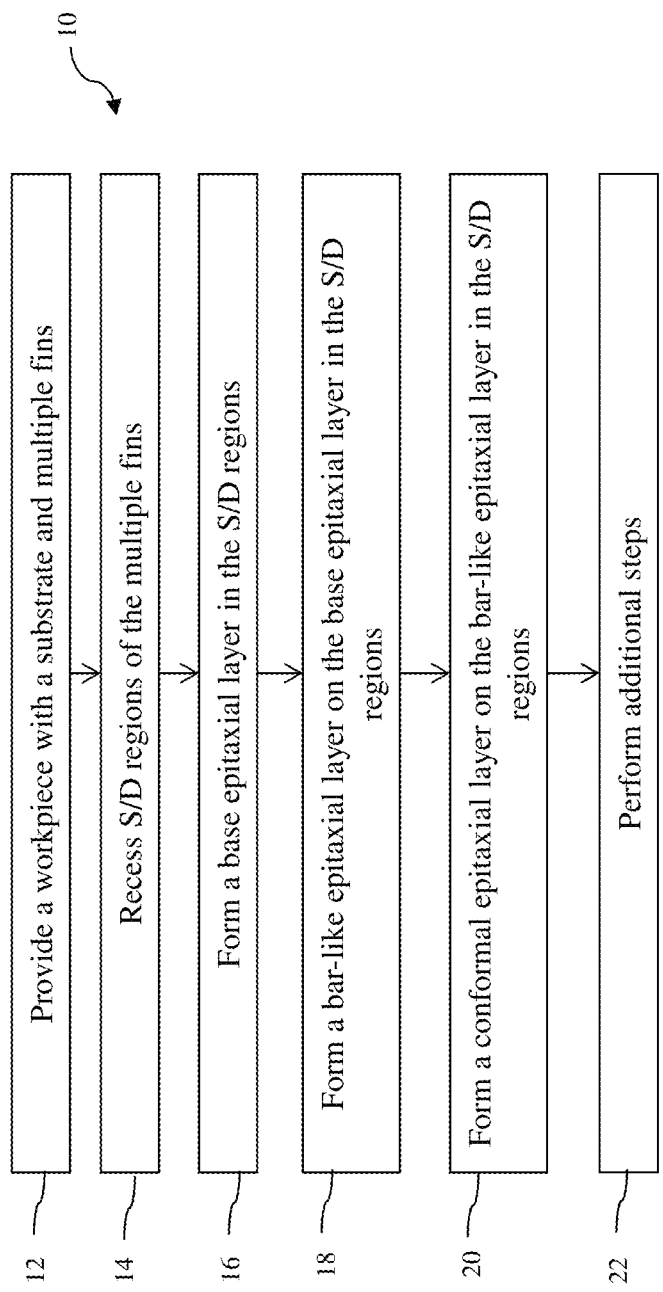
FIG. 1 is a flowchart of a method of fabricating a semiconductor device according to various embodiments of the present disclosure.

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. Moreover, the formation of a feature connected to and/or coupled to another feature in the present disclosure that follows may include embodiments in which the features are formed in direct contact, and may also include embodiments in which additional features may be formed interposing the features, such that the features may not be in direct contact.

In addition, the present disclosure may repeat reference numerals and/or letters in the various examples. This repetition is for the purpose of simplicity and clarity and does not in itself dictate a relationship between the various embodiments and/or configurations discussed. Moreover, the formation of a feature on, connected to, and/or coupled to another feature in the present disclosure that follows may include embodiments in which the features are formed in direct contact, and may also include embodiments in which additional features may be formed interposing the features, such that the features may not be in direct contact. In addition, spatially relative terms, for example, "lower," "upper," "horizontal," "vertical," "above," "over," "below," "beneath," "up," "down," "top," "bottom," etc. as well as derivatives thereof (e.g., "horizontally," "downwardly," "upwardly," etc.) are used for ease of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/−10% of the number described or other values as understood by person skilled in the art. For example, the term "about 5 nm" encompasses the dimension range from 4.5 nm to 5.5 nm.

The present disclosure is generally related to formation of source/drain features of FETs, and more particularly, to formation of source/drain features to reduce parasitic capacitance and lower contact resistance. In this regard, the present disclosure discloses a method to form source/drain features with more than one epitaxial layer and corresponding semiconductor devices. In some example, the method includes forming a bar-like epitaxial layer to reduce the projection area of the source/drain feature on a gate structure while maintaining the height of the source/drain feature. In some other examples, the method includes forming a conformal epitaxial layer over the bar-like epitaxial layer to form a flat top surface of the projection area. The reduced projection area of the source/drain feature on the gate structure reduces parasitic capacitance and the flat top surface of the projection area facilitates contact with the source/drain contact. In addition, the formation of bar-like epitaxial layer avoids the need to implement higher fin side walls, which may lead to increased resistance.

FIG. 1 illustrates a flowchart of a method 10 for forming a semiconductor device on a workpiece 100 (illustrated in FIGS. 2-8) in accordance with some embodiments of the present disclosure. The method 10 is merely an example and is not intended to limit the present disclosure beyond what is explicitly recited in the claims. Additional operations may be performed before, during, and after the method 10, and some operations described can be replaced, eliminated, or moved around for additional embodiments of the method 10. The method 10 is described below in conjunction with FIGS. 2~8, which illustrate various diagrammatic perspective and cross-sectional views of the semiconductor device on the workpiece 100 during intermediate steps of the method 10. In particular, FIG. 2 illustrates a diagrammatic perspective view of the semiconductor device on the workpiece 100 and FIGS. 3~8 illustrate diagrammatic cross-sectional views of the semiconductor device on the workpiece 100 taken along line A-A' as shown in FIG. 2.

The semiconductor device on the workpiece 100 may be an intermediate device fabricated during processing of an integrated circuit (IC), or a portion thereof, that may comprise static random-access memory (SRAM) and/or other logic circuits, passive components such as resistors, capacitors, and inductors, and active components such as p-type FETs (PFETs), n-type FETs (NFETs), fin-like FETs (FIN-FETs), metal-oxide semiconductor field effect transistors (MOSFET), complementary metal-oxide semiconductor (CMOS) transistors, bipolar transistors, high voltage transistors, high frequency transistors, and/or other memory cells The present disclosure is not limited to any particular number of devices or device regions, or to any particular device configurations. For example, though the semiconductor device on the workpiece 100 as illustrated is a three-dimensional FET device (e.g., a FINFET or a gate-all-around (GAA) FET), the present disclosure may also provide embodiments for fabricating planar FET devices.

Figure 2:
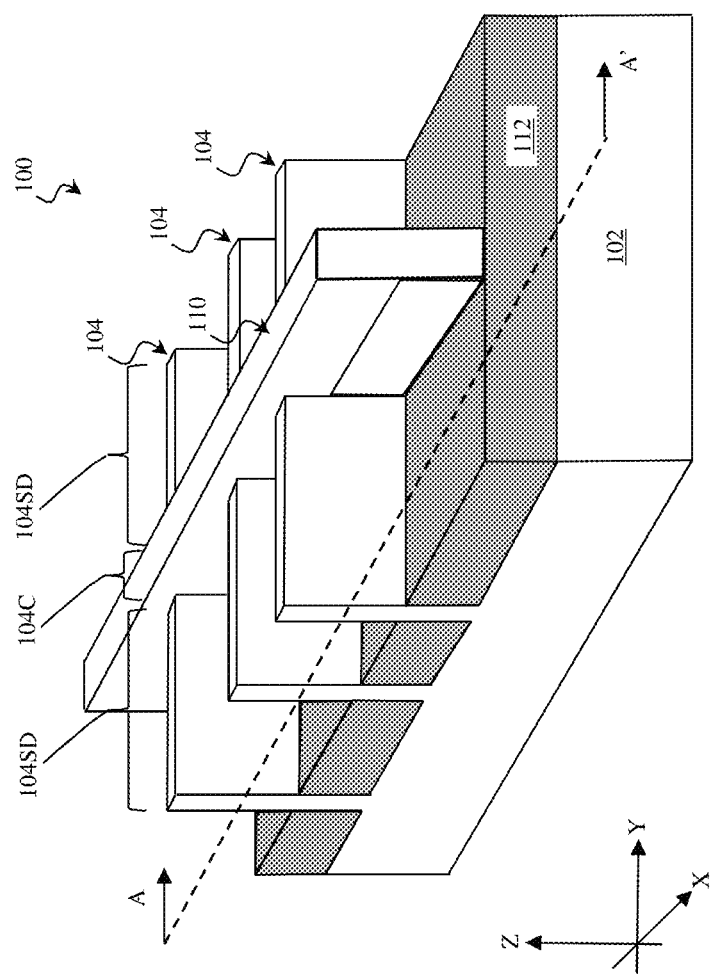
FIG. 2 is a diagrammatic perspective view of a workpiece that includes source/drain features according to various embodiments of the present disclosure.
Figure 3:
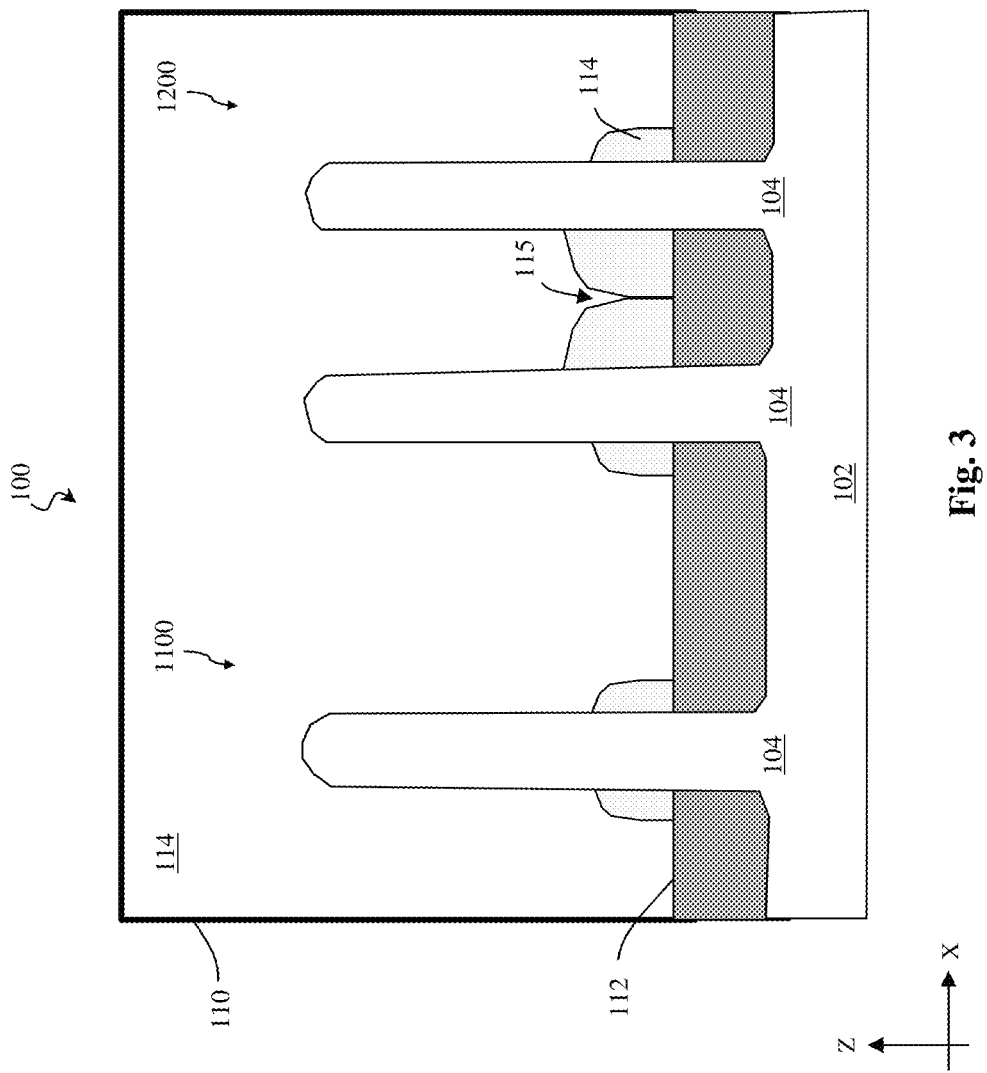
FIGS. 3~7 are diagrammatic cross-sectional views of source/drain features on a workpiece at various stages of fabrication according to various embodiments of the present disclosure.

Referring now to the method 10 in FIG. 1 and FIGS. 2 and 3, the method 10 includes a block 12 where a workpiece 100, which includes a substrate 102 and multiple fins 104, is provided. The workpiece 100 is received that includes a substrate 102 that represents any structure upon which circuit devices (such as semiconductor devices, transistor devices, FinFETs) may be formed. In various examples, the substrate 102 includes an elementary (single element) semiconductor, such as silicon or germanium in a crystalline structure; a compound semiconductor, such as silicon carbide, gallium arsenic, gallium phosphide, indium phosphide, indium arsenide, and/or indium antimonide; an alloy semiconductor such as SiGe, GaAsP, AlInAs, AlGaAs, GaInAs, GaInP, and/or GaInAsP; a non-semiconductor material, such as soda-lime glass, fused silica, fused quartz, and/or calcium fluoride (CaF2); and/or combinations thereof. The substrate 102 may be uniform in composition or may include various layers, some of which may be selectively etched to form the fins. The layers may have similar or different compositions, and in various embodiments, some substrate layers have non-uniform compositions to induce device strain and thereby tune device performance. Examples of layered substrates include silicon-on-insulator (SOI) substrates 102. In some such examples, a layer of the substrate 102 may include an insulator such as a semiconductor oxide, a semiconductor nitride, a semiconductor oxynitride, a semiconductor carbide, and/or other suitable insulator materials.

Doped regions, such as wells, may be formed on the substrate 102. In that regard, some portions of the substrate 102 may be doped with p-type dopants, such as boron, $BF_2$, or indium while other portions of the substrate 102 may be doped with n-type dopants, such as phosphorus or arsenic; and/or other suitable dopants including combinations thereof.

In some examples, the devices to be formed on the substrate 102 extend out of the substrate 102. For example, FinFETs and/or other non-planar devices may be formed on fins 104 disposed on the substrate 102. The fins 104 are representative of any raised feature and include FinFET device fins 104 as well as fins 104 for forming other raised active and passive devices upon the substrate 102. The fins 104 may be similar in composition to the substrate 102 or may be different therefrom. For example, in some embodiments, the substrate 102 may include primarily silicon, while the fins 104 include one or more layers that are primarily germanium or a SiGe semiconductor. In some embodiments, the substrate 102 includes a SiGe semiconductor, and the fins 104 include a SiGe semiconductor with a different ratio of silicon to germanium than the substrate 102.

The fins 104 may be formed by etching portions of the substrate 102, by depositing various layers on the substrate 102 and etching the layers, and/or by other suitable techniques. For example, the fins 104 may be patterned using one or more photolithography processes, including double-patterning or multi-patterning processes. Generally, double-patterning or multi-patterning processes combine photolithography and self-aligned processes, allowing patterns to be created that have, for example, pitches smaller than what is otherwise obtainable using a single, direct photolithography process. For example, in one embodiment, a sacrificial layer is formed over the fins 104 and is patterned using a photolithography process. Spacers are formed alongside the patterned sacrificial layer using a self-aligned process. The sacrificial layer is then removed, and the remaining spacers are used to pattern the fins 104 by removing material of the substrate 102 that is not covered by the spacers so that the fins 104 remain.

The fins 104 may include source/drain features formed over the source/drain regions 104SD and channel regions 104C disposed between the source/drain regions 104SD. The source/drain features and the channel regions 104C may be doped to be of opposite type. For an n-channel device, the source/drain features are doped with an n-type dopant and the channel region 104C is doped with a p-type dopant, and vice versa for an p-channel device.

One or more gate structures 110 may be disposed above and alongside the channel regions 104C. The flow of carriers (electrons for an n-channel device and holes for a p-channel device) through the channel region 104C between the source/drain regions 104SD is controlled by a voltage applied to the gate structures 110. In some embodiments, the one or more gate structures 110 may be dummy gate structures that include dummy gate dielectric layers and dummy gate electrodes. In some instances, the dummy gate dielectric layers may include a semiconductor oxide, such as silicon oxide, and the dummy gate electrodes may include polycrystalline semiconductor, such as polysilicon. In those embodiments, the dummy gate structures are to be removed and replaced with functional gate structures, such as metal gate structures that include high-k gate dielectric layers and metal gate electrodes. In those embodiments, the high-k gate dielectric layers may include high-k dielectric materials (having a dielectric constant greater than that of silicon oxide) such as hafnium oxide, tantalum oxide, titanium oxide, lanthanum oxide, zirconium oxide, aluminum oxide or a combination thereof. In some other embodiments, the one or more gate structures 110 may be functional gate structures that are not to be removed and replaced at a later stage. While not shown in FIG. 2 for simplicity, a gate spacer 114 may be formed over sidewalls of the one or more gate structures 110 and over sidewalls of the fins 104, as illustrated in FIG. 3. The gate spacer 114 may be used to offset the subsequently formed source/drain features and may be used for designing or modifying the source/drain feature profile. The gate spacer 114 may include any suitable dielectric material, such as a semiconductor oxide, a semiconductor nitride, a semiconductor carbide, a semiconductor oxynitride, other suitable dielectric materials, and/or combinations thereof. The gate spacer 114 may include multiple films, such as two films (a silicon oxide film and a silicon nitride film) or three films (a silicon oxide film; a silicon nitride film; and a silicon oxide film). The formation of the gate spacer 114 includes deposition and anisotropic etching, such as dry etching. In some implementations shown in FIG. 3, the gate spacer 114 formed between two adjacent fins 104 may partially merge or be in contact at an interface 115. In some instances, a slit may form at the interface 115. In addition, because the gate spacer 114 between two adjacent fins 104 may experience slower etch rate, gate spacer 114 between two adjacent fins 104 may have a height along the Z direction that is greater than a height of gate spacer 114 not disposed between two adjacent fins 104.

The source/drain features, once formed, are separated from the gate structures 110 (or the functional gate structure replacing the gate structures 110 if gate structures 110 are dummy gate structures) by the gate spacer 114. In this regard, the source/drain feature, the gate spacer 114, and the gate structure 110 constitute a parasitic capacitor, with the source/drain feature and the gate structure 110 functioning as electrodes of the parasitic capacitor. The capacitance of the parasitic capacitor is proportional to the overlapping area between the source/drain feature and the gate structure 110 and reversely proportional to the thickness of the gate spacer 114. As the thickness of the gate spacer 114 shrinks in the down-scaling of semiconductor devices, the parasitic capacitor may harness sufficient capacitance to impact switching speed of the pertinent transistors. With a given thickness of the gate spacer 114, the capacitance of the parasitic capacitor may be determined by the overlapping area between the source/drain feature and the gate structure 110. Because the gate structure 110 is generally larger than the projection area of the source/drain feature on the gate structure 110, the capacitance of the parasitic capacitor is governed by the projection area of the source/drain feature on the gate structure 110. One of the purposes of the present disclosure is to reduce the projection area of the source/drain feature on the gate structure 110.

The workpiece 100 may also include an isolation dielectric layer 112 disposed on the substrate 102 between the fins 104 to form isolation features (e.g., Shallow Trench Isolation features (STIs)). The isolation dielectric layer 112 may include a dielectric material such as a semiconductor oxide, a semiconductor nitride, a semiconductor oxynitride, a semiconductor carbide, a semiconductor carbonitride, a semiconductor oxycarbonitride, a metal oxide, etc., and in some examples, the isolation dielectric layer 112 includes multiple sublayers of different dielectric materials. The isolation dielectric layer 112 may be formed by any suitable process, and in some examples, the isolation dielectric layer 112 is deposited using Atomic Layer Deposition (ALD), Plasma Enhanced ALD (PEALD), Chemical Vapor Deposition (CVD), Plasma Enhanced CVD (PECVD), High-Density Plasma CVD (HDP-CVD), and/or other suitable deposition processes. Following deposition, the isolation dielectric layer 112 may be etched back so that the uppermost portions of the fins 104 protrude above the isolation dielectric layer 112. In various such examples, the fins 104 extend between about 20 nm and about 100 nm above the topmost surface of the isolation dielectric layer 112.

Figure 4:
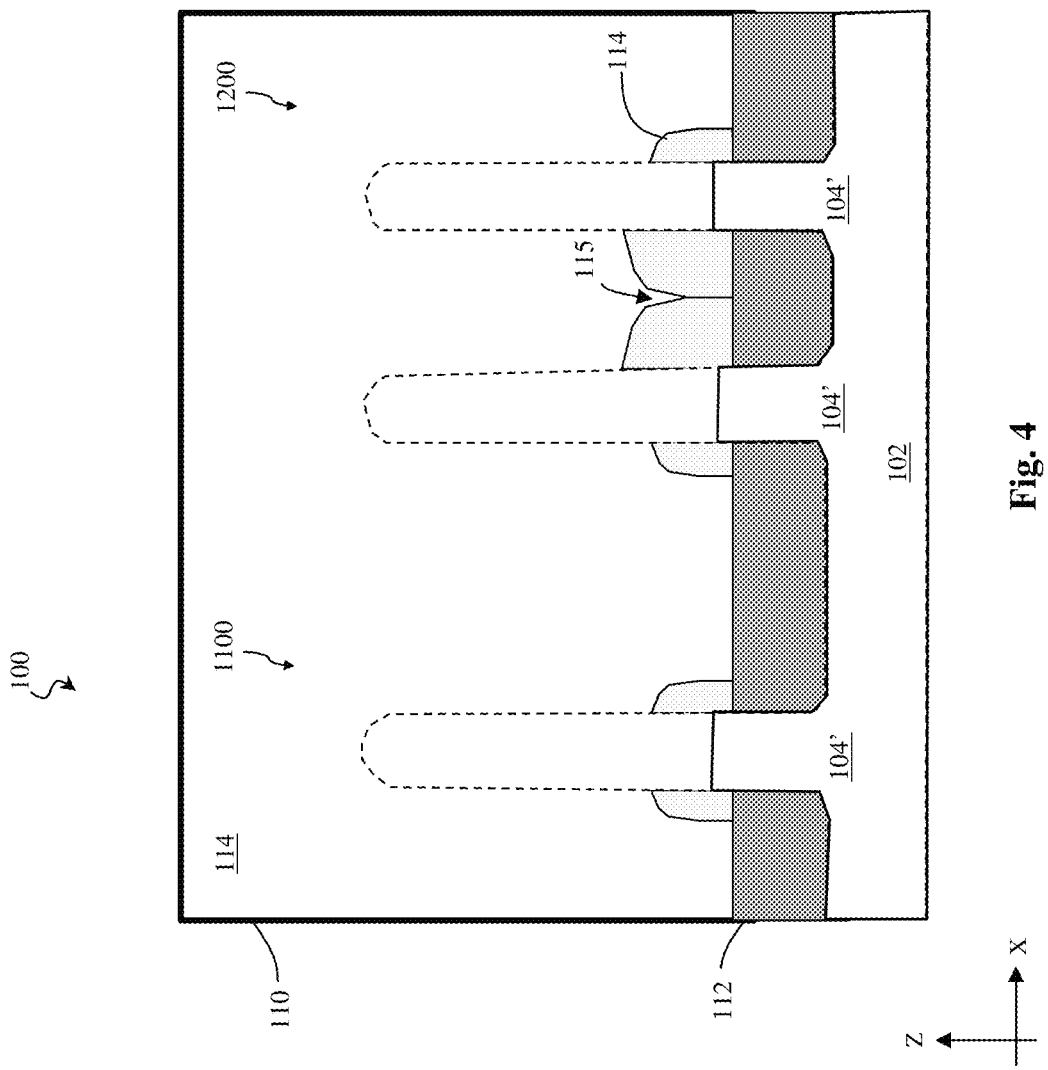

Referring now to the method 10 in FIG. 1 and FIG. 4, the method 10 includes a block 14 where source/drain regions 104SD of the multiple fins 104 are recessed. At block 14, upper portions of the multiple fins 104 are removed, leaving the lower portions of the multiple fins 104' in the source/drain regions 104SD. In some embodiments, the source/drain regions 104SD of the fins 104 are recessed using a suitable etching process, such as a dry etching process, a wet etching process, or a reactive-ion etching (RIE) process. In some implementations, block 14 of method 10 etches the fins 104 while other structures, such as gate structures 110, are masked off by hard masks or gate spacers and are not etched (or substantially not etched). The etching process at block 14 may implement a dry etch process using an etchant including a bromine-containing gas (e.g., HBr and/or CHBR3), a fluorine-containing gas (e.g., CF4, SF6, CH2F2, CHF3, and/or C2F6), other suitable gases, or combinations thereof. The recess of the fins may be controlled by adjusting conditions such as pressure, temperature, and the duration of the etching process. In some embodiments, the etching uses an etchant including HBr and CF4, under a pressure between about 5 and about 30 millitorr, and at a temperature between about 30° C. and about 60° C. In some embodiments, the etching lasts for about 5 to about 10 seconds. In some embodiments, as shown in FIG. 4, the etching process at block 14 removes upper portions of the fins 104 such that top surfaces of the recessed fins 104' are either even with top surfaces of the gate spacers 114 or about 0 nm to 15 nm below top surfaces of the gate spacers 114. As will be explained below with respect to the second and third epitaxial layers, it may be undesirable when the top surfaces of the recessed fins 104' are more than 5 nm below the top surfaces of the gate spacers 114, as contact resistance with the source/drain contact may increase due to insufficient thickness of heavily doped epitaxial layers (i.e. the conformal epitaxial feature 106C, to be described below).

Figure 5:
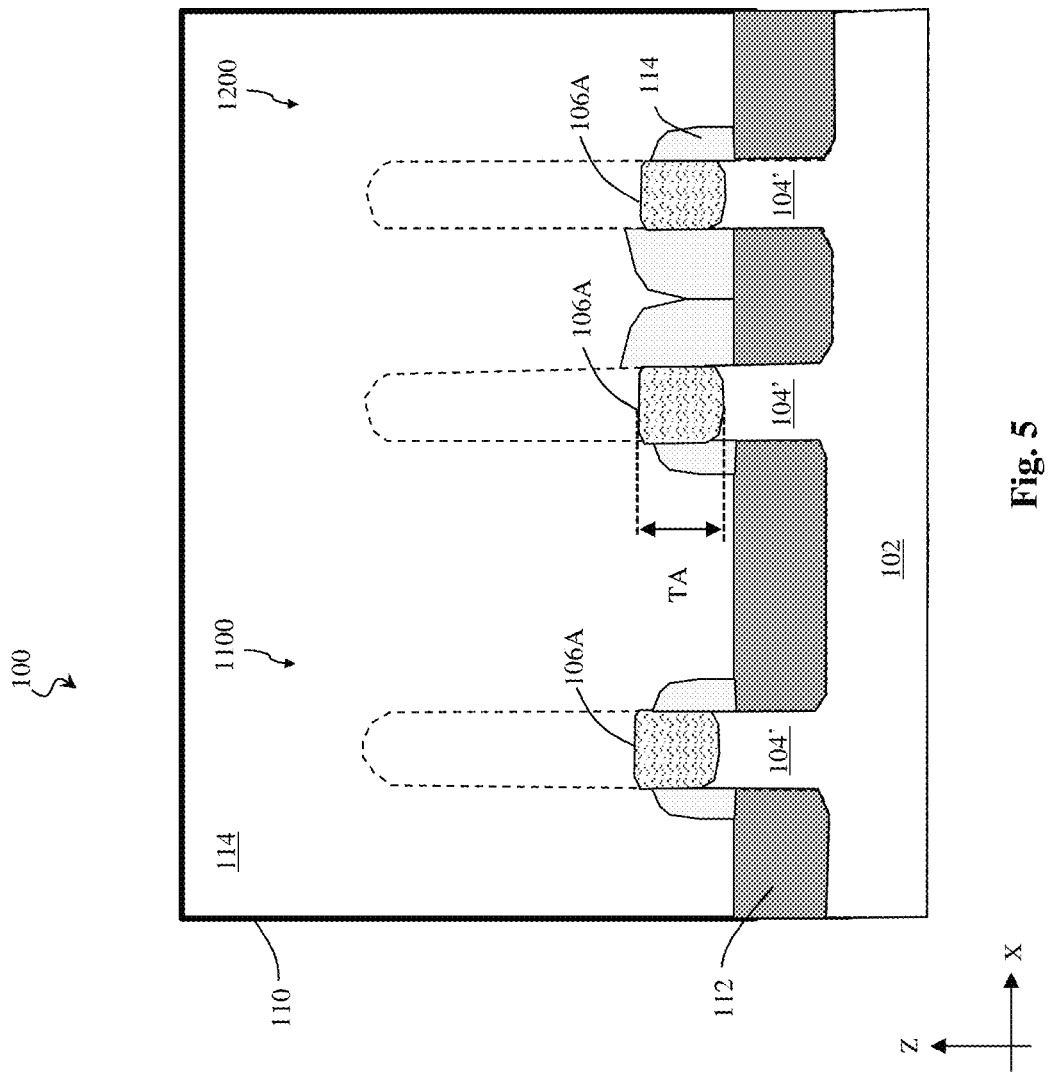

Referring now to the method 10 in FIG. 1 and FIG. 5, the method 10 includes a block 16 where a first epitaxial layer 106A is formed on the recessed fins 104' in the source/drain regions 104SD. In some implementations, because the first epitaxial layer 106A is grown on the recessed fins 104', it may also be referred to as a base epitaxial feature 106A. In some embodiments, the first epitaxial layer 106A may be epitaxially grown using a suitable technique, such as vapor-phase epitaxy (VPE), ultra-high vacuum CVD (UHV-CVD), a cyclic deposition and etching (CDE) process, molecular beam epitaxy (MBE), and/or other suitable processes. The epitaxy process may use gaseous and/or liquid precursors, which interact with the composition of the recessed fins 104'. In some embodiments, block 16 may use a single silicon gaseous species as the source of silicon. In some instances, block 16 uses only silane ($SiH_4$) or only dichlorosilane ($SiCl_2H_2$). In some implementations, the first epitaxial layer 106A is formed in an n-type device region and is in-situ doped with an n-type dopant, such as phosphorous and arsenide, at a first doping concentration. For example, arsine ($AsH_3$) or phosphine ($PH_3$) may be used to dope the first epitaxial layer 106A and the flow rate of arsine or phosphine may be increased or decrease to control the first doping concentration. In some instances, the first doping concentration is between $5 \times 10^{20}$ atoms per $cm^3$ and $3 \times 10^{21}$ atoms per $cm^3$. In some implementations, one or more recess (etch back) of the first epitaxial layer 106A may be performed during and after the formation of the first epitaxial layer 106A. As the first epitaxial layer 106A is substantially formed within the cavity left behind by removed portion of fins 104, the width of the first epitaxial layer 106A along the X direction may be limited to the width of the fins 104 along the X direction. The first epitaxial layer 106A has a doping concentration higher than that of the fin 104 and serves as a doping concentration transition portion between the fin 104 and even more heavily doped epitaxial layers to be formed on the first epitaxial layer 106A. The first epitaxial layer 106A has a thickness TA measured from a top surface of the recessed fin 104'. The thickness TA of the first epitaxial layer 106A may be minimized such that the thicknesses of heavily doped epitaxial layers of the first epitaxial layer 106A can be maximized for purposes of reducing contact resistance. That said, the thickness TA of the first epitaxial layer 106A may not be so small as it needs a reasonable number of single layers to serve its transitional function. In some embodiments, the thickness TA may be between about 4 nm and about 5 nm.

Figure 6:
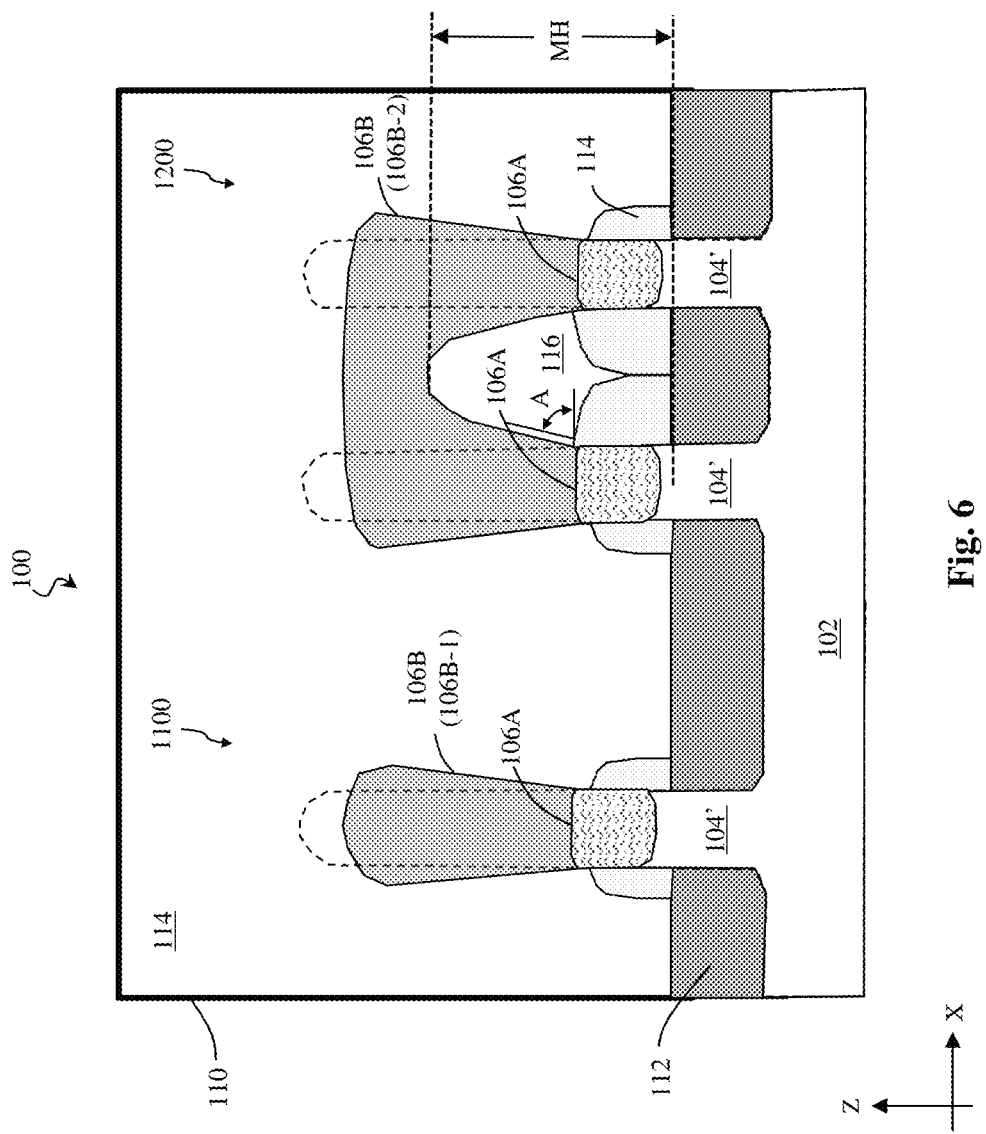

Referring now to the method 10 in FIG. 1 and FIG. 6, the method 10 includes a block 18 where a second epitaxial layer 106B is formed on the first epitaxial layer 106A. In some implementations, because the second epitaxial layer 106B is intended to grow faster along the Z direction (normal to the top surface of the substrate 102) and has a more elongated shape than conformal epitaxial features, it may also be referred to as a bar-like epitaxial feature 106B. In some embodiments, the second epitaxial layer 106B may be epitaxially grown using a suitable technique, such as VPE, CDE, UHV-CVD, or MBE. Different from the operations at block 16, the growth rate of the second epitaxial layer 106B is intentionally made slower such that epitaxy is preferentially formed on the (100) plane of the substrate. In some embodiments, a top-facing surface of the substrate 102 includes the (100) plane (i.e. Z direction is normal to the (100) plane of the substrate) and the fins 104 also include top-facing surfaces that include the (100) plane. At block 18, because the slower epitaxy growth rate, epitaxy happens faster on the (100) plane and allows the second epitaxial layer 106B to be more bar-like. In some embodiments, Le Chatelier's Principle is utilized to achieve selective epitaxy growth on the (100) plane. In one example, instead of using only silane or only dichlorosilane at block 16, both silane and dichlorosilane are used as precursors at block 18 to form the second epitaxial layer 106B. In that example, at least the following chemical reactions may take place during the epitaxy process: (1) $SiH_2Cl_2 \leftrightarrows SiCl_2 + H_2$; (2) $SiCl_2 + H_2 \leftrightarrows Si + 2HCl$; (3) $SiH_4 \leftrightarrows Si + 2H_2$; and (4) $SiHCl_3 \leftrightarrows SiCl_2 + HCl$. In reactions (2) and (3) where Si is a product of the reaction, the presence of $H_2$ and HCl, which are products of reactions (1) and (4), may move the equilibrium to the left and slows down the epitaxy growth of silicon for selective growth on the (100) plane. In some other examples, the partial pressure of HCl may be dynamically controlled at block 18 to further control the formation of the second epitaxial layer 106B.

Referring still to FIG. 6, the bar-like epitaxial feature 106B may be formed over the source/drain region 104SD of a single-fin device 1100 or over the source/drain region 104SD of a double-fin device 1200. While not shown in FIG. 6 for simplicity, the bar-like epitaxial feature 106B may also be formed over the source/drain region of a multi-fin device with more than two fins. For ease of reference, the bar-like epitaxial feature 106B of the single-fin device 1100 may be referred to as the first bar-like epitaxial feature 106B-1 and the bar-like epitaxial feature 106B of the double-fin device 1200 may be referred to as the second bar-like epitaxial feature 106B-2. The second bar-like epitaxial feature 106B-2 includes two branches extending from two recessed fins 104'. The two branches gradually become wider along the X direction as they extend away from the substrate and finally merge at roughly half-way between the two recessed fins 104'. In some instances, the second bar-like epitaxial feature 106B-2, the gate spacers 114, and the isolation dielectric layer 112 define an air gap 116. In some other instances, the two recessed fins 104' may be so adjacent that the gate spacers 114 between the two recessed fins 104' merge or are in contact with one another. The gap 116 has a peak gap height (or merge height) MH. In some embodiments, the peak gap height MH is between about 30 nm and about 40 nm. In some instances, the second bar-like epitaxial feature 106B-2 extends from the gate spacer 114 at an angle A with respect to the top surface of the isolation dielectric layer 112. The angle A is between about 65° and about 80°, which is greater than similar situated angles in conventional merged epitaxial features. The angle A governs how much the second bar-like epitaxial feature 106B-2 thickens along the X direction as the second bar-like epitaxial feature 106B-2 gains height along the Z direction. For example, when the angle A is about 65°, the second bar-like epitaxial feature 106B-2 thickens along the X direction by about 0.92 nm as the second bar-like epitaxial feature 106B-2 grows 1 nm long the Z direction. For another example, when the angle A is about 80°, the second bar-like epitaxial feature 106B-2 thickens along the X direction by about 0.35 nm as the second bar-like epitaxial feature 106B-2 grows 1 nm long the Z direction.

In some implementations, the second epitaxial layer 106B in FIG. 6 is formed in an n-type device region and is in-situ doped with an n-type dopant, such as phosphorous and arsenide, at a second doping concentration greater than the first doping concentration of the first epitaxial layer 106A. For example, arsine ($AsH_3$) or phosphine ($PH_3$) may be used to dope the second epitaxial layer 106B and the flow rate of arsine or phosphine may be increased or decrease to control the second doping concentration. In some instances, the second doping concentration is between $3 \times 10^{21}$ atoms per $cm^3$ and $4 \times 10^{21}$ atoms per $cm^3$. In some implementations, one or more recess (etch-back) of the second epitaxial layer 106B may be performed during and after the formation of the second epitaxial layer 106B.

Figure 7:
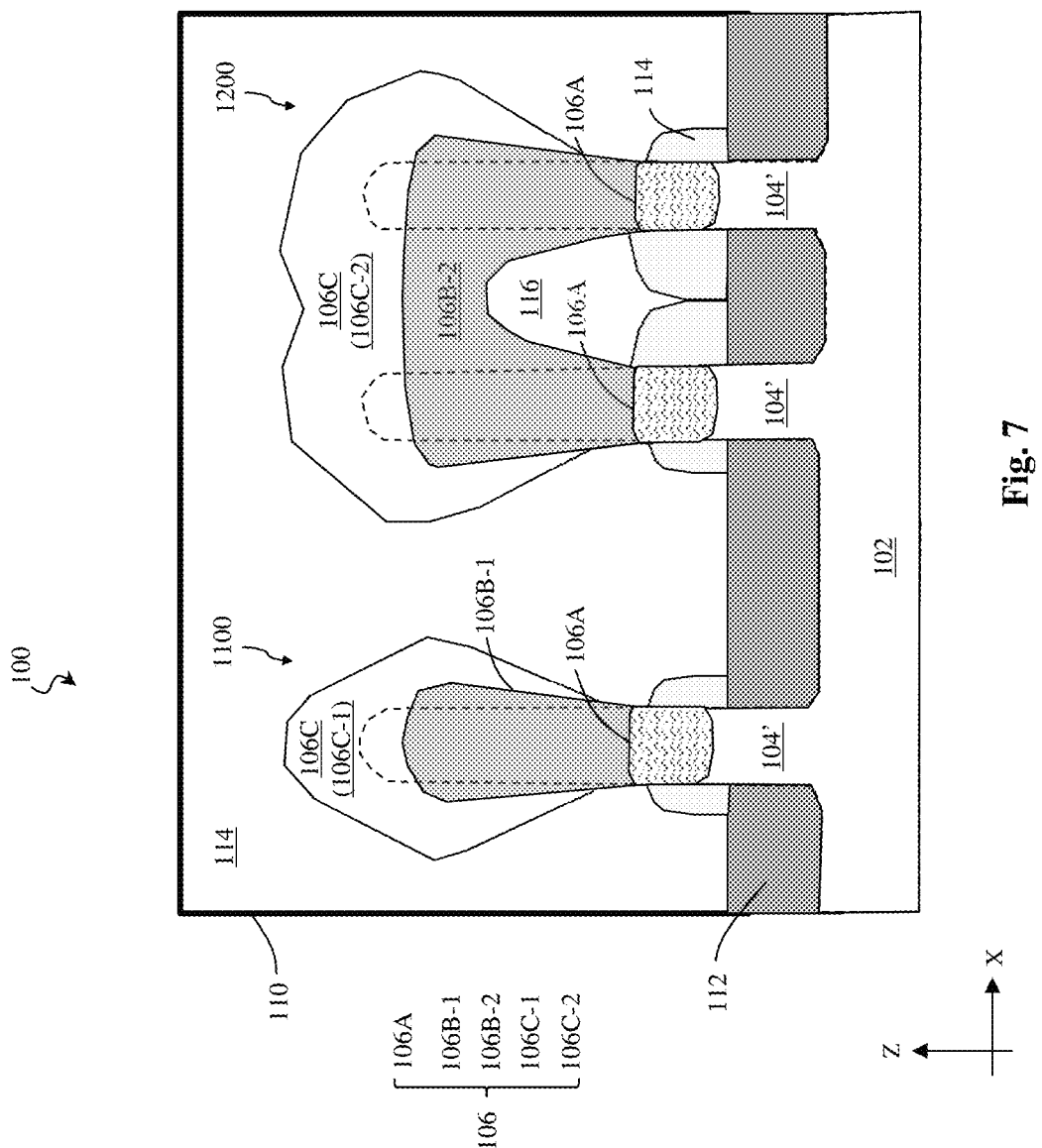

Referring now to the method 10 in FIG. 1 and FIG. 7, the method 10 includes a block 20 where a third epitaxial layer 106C is formed on the second epitaxial layer 106B. In some implementations, because the third epitaxial layer 106C is intended to grow conformally over the second epitaxial layer 106B along all directions, it may also be referred to as a conformal epitaxial feature 106C. In some embodiments, the third epitaxial layer 106C may be epitaxially grown using a suitable technique, such as VPE, UHV-CVD, CDE, or MBE. Similar to operations at block 16, the growth rate of the third epitaxial layer 106C is uniform along all direction and is not selective to the (100) plane. As shown in FIG. 7, the conformal epitaxial feature 106C may be formed over the source/drain region 104SD of the single-fin device 1100 or over the source/drain region 104SD of the double-fin device 1200. While not shown in FIG. 7 for simplicity, the conformal epitaxial feature 106C may also be formed over the source/drain region of a multi-fin device with more than two fins. For ease of reference, the conformal epitaxial feature 106C of the single-fin device 1100 may be referred to as the first conformal epitaxial feature 106C-1 and the conformal epitaxial feature 106C of the double-fin device 1200 may be referred to as the second conformal epitaxial feature 106C-2. Because the epitaxy growth at block 20 is conformal and omnidirectional (along all directions), the first conformal epitaxial feature 106C-1 is wider than the first bar-like epitaxial feature 106B-1 and the second conformal epitaxial feature 106C-2 is wider than the second bar-like epitaxial feature 106B-2. In some implementations, the third epitaxial layer 106C in FIG. 7 is formed in an n-type device region and is in-situ doped with an n-type dopant, such as phosphorous and arsenide, at a third doping concentration greater than the second doping concentration of the second epitaxial layer 106B. For example, arsine ($AsH_3$) or phosphine ($PH_3$) may be used to dope the third epitaxial layer 106C and the flow rate of arsine or phosphine may be increased or decrease to control the third doping concentration. In some instances, the third doping concentration is between $4\times10^{21}$ atoms per $cm^3$ and $5\times10^{21}$ atoms per $cm^3$. In some implementations, one or more recess (etch back) of the third epitaxial layer 106C may be performed during and after the formation of the third epitaxial layer 106C. The first epitaxial layer 106A, the second epitaxial layer 106B and the third epitaxial layer 106C together constitute the epitaxial feature 106 (or source/drain feature 106) and may be referred to accordingly.

Referring now to the method 10 in FIG. 1, the method 10 includes a block 22 where further processes are performed. For example, after all layers of the epitaxial feature 106 has been formed, an interlayer dielectric (ILD) layer may be deposited over the workpiece 100, including over the epitaxial feature 106 (or source/drain feature 106). For another example, a via hole may be formed through the ILD layer to expose the epitaxial feature 106 and a conductive material may be deposited in the via hole to form the source/drain contact. In some implementations, a contact etch stop layer (CESL) may be formed between the ILD layer and the source/drain feature 106. In some embodiments, a silicide layer may be formed over the source/drain feature 106 exposed in the via hole and one or more barrier layer may be formed over sidewall of the via hole to prevent oxidation of the conductive material. In some instances, the CESL may be formed of silicon nitride that may or may not be doped with carbon. The silicide layer may include nickel silicide, tungsten silicide or titanium silicide and may be formed by depositing a metal layer over the source/drain feature 106, annealing the metal layer such that the metal layer reacts with silicon in the epitaxial features 106 to form the metal silicidation, and thereafter removing the non-reacted metal layer. The conductive material may include a seed metal layer and a fill metal layer. In various embodiments, the seed metal layer includes cobalt (Co), tungsten (W), ruthenium (Ru), nickel (Ni), other suitable metals, or combinations thereof. The fill metal layer may include copper (Cu), tungsten (W), aluminum (Al), cobalt (Co), other suitable materials, or combinations thereof.

Figure 8:
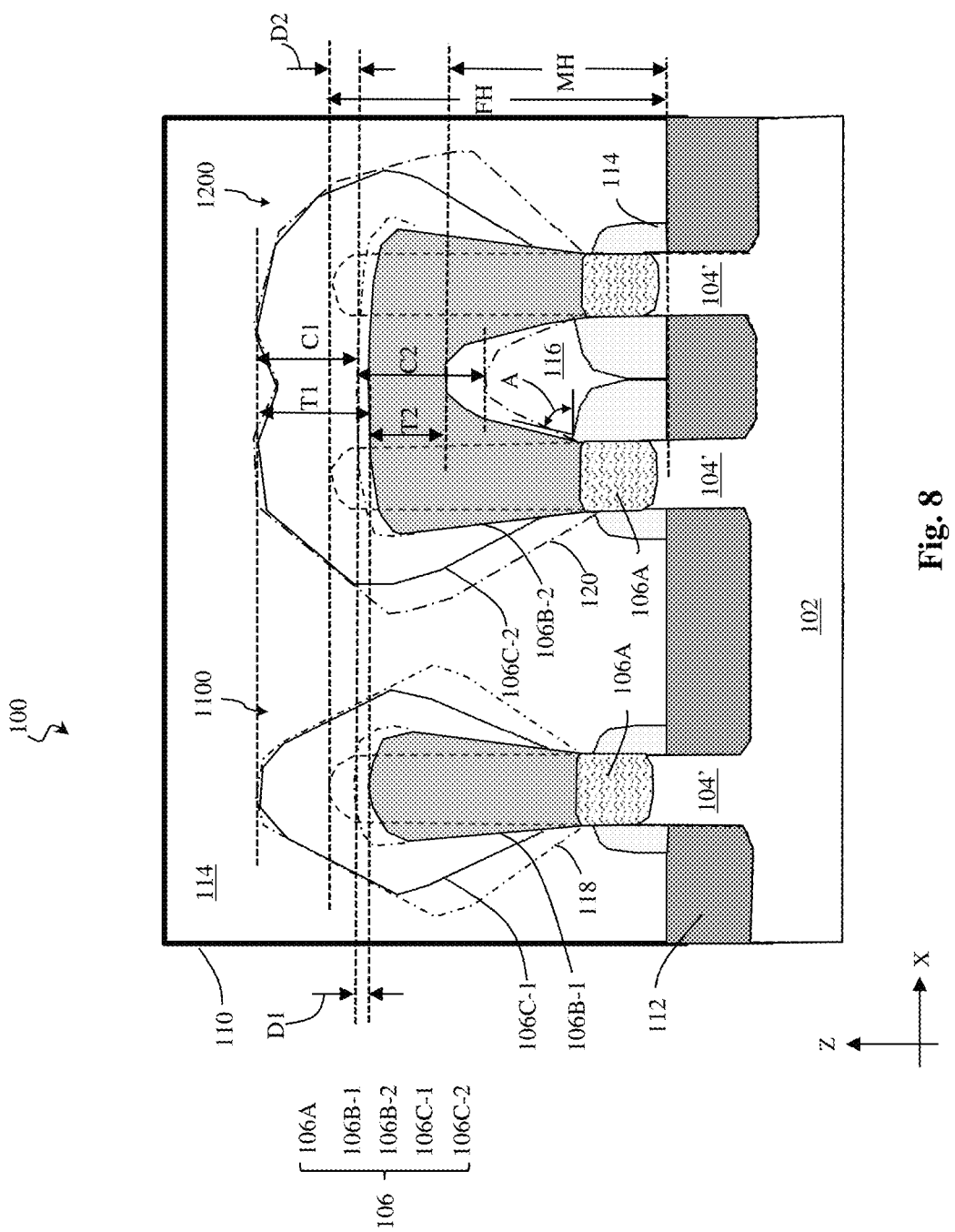
FIG. 8 is a diagrammatic cross-sectional view of source/drain features fabricated according to various embodiments of the present disclosure.

Referring now to FIG. 8, illustrated therein is a comparison of source/drain features 106 formed according to method 10 of the present disclosure against ones formed using a conventional method. FIG. 8 illustrates a first conventional source/drain feature 118 formed in the source/drain region 104SD of the single-fin device 1100 and a second conventional source/drain feature 120 formed in the source/drain region 104SD of the double-fin device 1200. The projection area of the first conventional source/drain feature 118 on the gate structure 110 is larger than that of the source/drain feature 106 (including the first epitaxial layer 106A, the first bar-like epitaxial feature 106B-1, and the first conformal epitaxial feature 106C-1) in the source/drain region 104SD of the single-fin device 1100. Similarly, the projection area of the second conventional source/drain feature 120 on the gate structure 110 is larger than that of the source/drain feature 106 (including the first epitaxial layer 106A, the second bar-like epitaxial feature 106B-2, and the second conformal epitaxial feature 106C-2) in the source/drain region 104SD of the double-fin device 1200. This reduction in projection area of the source/drain feature may result in reduction of parasitic capacitance in the capacitor formed between the gate structure 110 (or the metal gate structure replacing the gate structure) and the source/drain feature. As illustrated in FIG. 8, the lower portions of the source/drain features 106 of the present disclosure are narrower than the conventional source/drain features 118 and 120 along the X direction.

In FIG. 8, while the fins 104 are recessed to form the recessed fins 104', the unetched fins 104 are still shown in dotted lines for ease of reference. Before the recess, the fins 104 have a fin height FH measured from the top surface of the isolation dielectric layer 112. In some embodiments, the fin height FH is between about 50 nm and about 60 nm and the peak gap height MH is between about 30 nm and about 40 nm. In these embodiments, the peak gap height MH is between about 55% and about 80% of the fin height FH. As a comparison, the second conventional source/drain feature 120 may also include a gap and has a conventional peak gap height that is less than 50% of the fin height FH. It is noted that to ensure process and design integration, the conventional source/drain features 118 and 120 and the source/drain features 106 of the present disclosure share substantially the same height, which may constitute a design constraint. That design constraint limits the ability to form a taller source/drain feature. To reduce contact resistance to the source/drain features, the topmost epitaxial layer, such as the third epitaxial layer 106C, has a doping concentration higher than lower epitaxial layer(s), such as the second epitaxial layer 106B. By not recessing the fins 104 to have a depth (distance) D1 lower than the top surface of the gate spacers 114, the second epitaxial layer 106B may merge earlier and lower the top surface thereof by distance D1, allowing more heavily doped third epitaxial layer 106C to be formed over the second epitaxial layer 106B. For example, when the gate spacer 114 (or fin sidewall) is higher than the top surface of the recessed fin 104' by distance D1, it roughly takes the second epitaxial layer 106B additional height growth D1 to sufficiently merge the second epitaxial layer 106B and the fin height FH is greater than the peak layer height of the top surface of the second epitaxial layer 106B by a distance D2. However, when the gate spacer 114 (or fin sidewall) is even with the top surface of the recessed fin 104', the merge of the second epitaxial layer 106B can take place earlier in the epitaxial growth process and the fin height FH is greater than the peak layer height of the top surface of the second epitaxial layer 106B by summation of the distance D1 and the distance D2 (D1+D2). In some embodiments, D1 is between about 0 nm and 6 nm and D1+D2 is between about 4 nm and 10 nm.

Put differently, the present disclosure provides a method that is geared toward maximizing the thickness of the third epitaxial layer 106C to lower contact resistance while the thickness of the second epitaxial layer 106B is well controlled. Referring still to FIG. 8, the third epitaxial layer 106C has a characteristic thickness T1 measured from a top surface of the second epitaxial layer 106B and the second epitaxial layer 106B has a characteristic thickness T2 measured from the top of the air gap 116. In some embodiments, T1 is between about 8 nm and about 14 nm and T2 is between about 4 nm and about 20 nm. A ratio of T1 to T2 may be between about 0.5 and about 2. In contrast, the third epitaxial layer of the conventional source/drain feature 120 has a characteristic thickness C1 and the second epitaxial layer of the conventional source/drain feature 120 has a characteristic thickness C2. In some embodiments, C1 is between about 4 nm and about 10 nm and C2 is between about 28 nm and about 34 nm. A ratio of C1 to C2 is between about 0.1 and about 0.4. As illustrated in FIG. 8, T1 is greater than C1 while T2 is smaller than C2. It can therefore be seen that methods of the present disclosure control and minimize the thickness of the second epitaxial layer 106B and maximize the thickness of the third epitaxial layer 106C, as compared to structures formed using conventional methods.

In some embodiments, the source/drain feature 106 is implemented in an n-type device region, such as a region for n-type FinFETs, in a semiconductor device that also include a p-type device region, such as a region for p-type FinFETs. In these embodiments, the p-type device region shares similarities with the n-type device region. For example, the p-type device region also includes a plurality of fins, isolation dielectric layers among the fins, and gate structures.

Although not intended to be limiting, one or more embodiments of the present disclosure provide many benefits to a semiconductor device and the formation thereof. The present disclosure provides methods of forming a source/drain feature that includes multiple epitaxial layers. The multiple epitaxial layers include different in-situ doping concentrations and includes a bar-like epitaxial feature. The implementation of the bar-like epitaxial feature reduces the projection area of the source/drain feature on the gate structure and thereby reduces parasitic capacitance. In addition, the method of the present application allows appropriate merge of epitaxial features at a lower height and increases the thickness of the topmost epitaxial feature with increased in-situ doping concentration. The greater thickness of the heavily doped topmost epitaxial layer reduces contact resistance to the source/drain feature. Accordingly, the source/drain features formed using the disclosed methods reduce both parasitic capacitance and contact resistance.

The present disclosure provides for many different embodiments. In one embodiment, a method is provided. A method includes recessing a fin extending from a substrate, forming a base epitaxial feature on the recessed fin, forming a bar-like epitaxial feature on the base epitaxial feature, and forming a conformal epitaxial feature on the bar-like epitaxial feature. The forming of the bar-like epitaxial feature includes in-situ doping the bar-like epitaxial feature with an n-type dopant at a first doping concentration. The forming of the conformal epitaxial feature comprises in-situ doping the conformal epitaxial feature with a second doping concentration greater than the first doping concentration.

In some embodiments, the forming of the base epitaxial feature includes in-situ doping the base epitaxial feature with the n-type dopant at a third doping concentration equal to or lower than the first doping concentration. In some implementations, the first doping concentration is between about $3\times10^{21}$ atoms per cm$^3$ and about $4\times10^{21}$ atoms per cm$^3$. In some instances, the second doping concentration is between about $4\times10^{21}$ atoms per cm$^3$ and about $5\times10^{21}$ atoms per cm$^3$. In some embodiments, the forming of the bar-like epitaxial feature includes using a plurality of silicon precursors comprising silane (SiH$_4$) and dichlorosilane (SiCl$_2$H$_2$). In some implementations, the forming of the conformal epitaxial feature includes using only dichlorosilane as a silicon precursor.

In another embodiment, a device is provided. The device includes a substrate, a plurality of fins extending from the substrate and each including a channel region, an isolation feature disposed on the substrate between the plurality of fins, spacers disposed on the isolation feature alongside the plurality of fins, and a source/drain feature disposed on the plurality of fins adjacent the channel region of the respective fin, and a gate structure disposed on the channel region. The source/drain feature includes a first layer disposed on each of the plurality of fins between the spacers, a second layer disposed on the first layer that extends above the spacers and spans the plurality of fins, wherein the second layer extends above the spacers at an angle between about 65° and about 80°, and a third layer disposed on the second layer that spans the plurality of fins.

In some embodiments, a top surface of the substrate comprises a (100) plane. In some embodiments, the second layer defines a gap extending between the second layer, the spacers, and the isolation feature, the gap has a peak gap height measured from a top surface of the isolation feature, the plurality of fins has a fin height measured from the top surface of the isolation feature, and the peak gap height is between about 55% and about 80% of the fin height. In some implementations, the second layer has a peak layer height measured from a top surface of the isolation feature, the plurality of fins has a fin height measured from the top surface of the isolation feature, and the fin height is greater than the peak layer height by a difference between about 1 nm and about 10 nm. In some instances, the first layer includes a semiconductor material and a dopant with a first dopant concentration and the second layer includes the semiconductor material and the dopant with a second dopant concentration greater than the first dopant concentration. In some implementations, the third layer includes the semiconductor material and the dopant with a third dopant concentration greater than the second dopant concentration. In some instance, the semiconductor material comprises silicon and the dopant is an n-type dopant, the second dopant concentration between about $3\times10^{21}$ atoms per cm$^3$ and about $4\times10^{21}$ atoms per cm$^3$, and the third layer dopant concentration between about $4\times10^{21}$ atoms per cm$^3$ and about $5\times10^{21}$ atoms per cm$^3$.

In yet another embodiment, a device is provided. The device includes a substrate, a first plurality of fins extending from the substrate in an n-type device region, wherein each of the first plurality of fins includes an n-type channel region, a second plurality of fins extending from the substrate in a p-type device region, wherein each of the second plurality of fins includes a p-type channel region, an isolation feature disposed on the substrate between the first plurality of fins and between the second plurality of fins, spacers disposed on the isolation feature alongside the first plurality of fins and alongside the second plurality of fins, a source/drain feature disposed on the first plurality of fins adjacent the n-type channel region of the respective fin, and a plurality of gate structures disposed on the n-type and p-type channel regions. The source/drain feature includes a first epitaxial layer disposed on each of the first plurality of fins between the spacers, a second epitaxial layer disposed on the first epitaxial layer that extends above the spacers and spans the first plurality of fins, wherein the second epitaxial layer extends above the spacers at an angle between about 65° and about 80°, and a third epitaxial layer disposed on the second epitaxial layer that spans the first plurality of fins.

In some embodiments, a top surface of the substrate comprises a (100) plane. In some implementations, the second epitaxial layer defines a gap extending between the second epitaxial layer, the spacers, and the isolation feature. The gap has a peak gap height measured from a top surface of the isolation feature. The first plurality of fins has a fin height measured from the top surface of the isolation feature and the peak gap height is between about 55% and about 80% of the fin height.

In some embodiments, the second epitaxial layer has a peak layer height measured from a top surface of the isolation feature, the first plurality of fins has a fin height measured from the top surface of the isolation feature, and the fin height is greater than the peak layer height by a difference between about 1 nm and about 10 nm. In some embodiments, the first epitaxial layer includes silicon and an n-type dopant with a first dopant concentration and the second epitaxial layer includes silicon and the n-type dopant with a second dopant concentration greater than the first dopant concentration. In some instances, the third epitaxial layer includes silicon and the n-type dopant with a third dopant concentration greater than the second dopant concentration. In some implementations, the n-type dopant includes arsenide or phosphorous, the second dopant concentration is between about $3 \times 10^{21}$ atoms per $cm^3$ and about $4 \times 10^{21}$ atoms per $cm^3$, and the third layer dopant concentration is between about $4 \times 10^{21}$ atoms per $cm^3$ and about $5 \times 10^{21}$ atoms per $cm^3$.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method comprising:
recessing a fin extending from a substrate;
forming a base epitaxial feature on the recessed fin;
forming a bar-like epitaxial feature on the base epitaxial feature; and
forming a conformal epitaxial feature on the bar-like epitaxial feature,
wherein the forming of the bar-like epitaxial feature comprises in-situ doping the bar-like epitaxial feature with an n-type dopant at a first doping concentration,
wherein the forming of the conformal epitaxial feature comprises in-situ doping the conformal epitaxial feature with a second doping concentration greater than the first doping concentration.

2. The method of claim 1, where the forming of the base epitaxial feature comprises in-situ doping the base epitaxial feature with the n-type dopant at a third doping concentration equal to or lower than the first doping concentration.

3. The method of claim 1, wherein the first doping concentration is between about $3 \times 10^{21}$ atoms per $cm^3$ and about $4 \times 10^{21}$ atoms per $cm^3$.

4. The method of claim 1, wherein the second doping concentration is between about $4 \times 10^{21}$ atoms per $cm^3$ and about $5 \times 10^{21}$ atoms per $cm^3$.

5. The method of claim 1, wherein the forming of the bar-like epitaxial feature comprises:
using a plurality of silicon precursors comprising silane ($SiH_4$) and dichlorosilane ($SiCl_2H_2$).

6. The method of claim 1, wherein the forming of the conformal epitaxial feature comprises:
using only dichlorosilane as a silicon precursor.

7. A device comprising:
a substrate;
a plurality of fins extending from the substrate, wherein each of the plurality of fins includes a channel region;
an isolation feature disposed on the substrate between the plurality of fins;
spacers disposed on the isolation feature alongside the plurality of fins;
a source/drain feature disposed on the plurality of fins adjacent the channel region of the respective fin, wherein the source/drain feature includes:
a first layer disposed on each of the plurality of fins between the spacers;
a second layer disposed on the first layer that extends above the spacers and spans the plurality of fins, wherein the second layer extends above the spacers at an angle between about 65° and about 80°; and
a third layer disposed on the second layer that spans the plurality of fins; and
a gate structure disposed on the channel region.

8. The device of claim 7, wherein a top surface of the substrate comprises a (100) plane.

9. The device of claim 7,
wherein the second layer defines a gap extending between the second layer, the spacers, and the isolation feature,
wherein the gap has a peak gap height measured from a top surface of the isolation feature,
wherein the plurality of fins has a fin height measured from the top surface of the isolation feature,
wherein the peak gap height is between about 55% and about 80% of the fin height.

10. The device of claim 7,
wherein the second layer has a peak layer height measured from a top surface of the isolation feature,
wherein the plurality of fins has a fin height measured from the top surface of the isolation feature,
wherein the fin height is greater than the peak layer height by a difference between about 1 nm and about 10 nm.

11. The device of claim 7,
wherein the first layer includes a semiconductor material and a dopant with a first dopant concentration,
wherein the second layer includes the semiconductor material and the dopant with a second dopant concentration greater than the first dopant concentration.

12. The device of claim 11,
wherein the third layer includes the semiconductor material and the dopant with a third dopant concentration greater than the second dopant concentration.

13. The device of claim 12,
wherein the semiconductor material comprises silicon and the dopant is an n-type dopant, wherein the second dopant concentration is between about $3 \times 10^{21}$ atoms per $cm^3$ and about $4 \times 10^{21}$ atoms per $cm^3$,
wherein the third layer dopant concentration is between about $4 \times 10^{21}$ atoms per $cm^3$ and about $5 \times 10^{21}$ atoms per $cm^3$.

14. A device comprising:
a substrate;
a first plurality of fins extending from the substrate in an n-type device region, wherein each of the first plurality of fins includes an n-type channel region;
a second plurality of fins extending from the substrate in a p-type device region, wherein each of the second plurality of fins includes a p-type channel region;
an isolation feature disposed on the substrate between the first plurality of fins and between the second plurality of fins;
spacers disposed on the isolation feature alongside the first plurality of fins and alongside the second plurality of fins;
a source/drain feature disposed on the first plurality of fins adjacent the n-type channel region of the respective fin, wherein the source/drain feature includes:
  a first epitaxial layer disposed on each of the first plurality of fins between the spacers;
  a second epitaxial layer disposed on the first epitaxial layer that extends above the spacers and spans the first plurality of fins, wherein the second epitaxial layer extends above the spacers at an angle between about 65° and about 80°; and
  a third epitaxial layer disposed on the second epitaxial layer that spans the first plurality of fins; and
a plurality of gate structures disposed on the n-type and p-type channel regions.

15. The device of claim 14, wherein a top surface of the substrate comprises a (100) plane.

16. The device of claim 14,
wherein the second epitaxial layer defines a gap extending between the second epitaxial layer, the spacers, and the isolation feature,
wherein the gap has a peak gap height measured from a top surface of the isolation feature,
wherein the first plurality of fins has a fin height measured from the top surface of the isolation feature,
wherein the peak gap height is between about 55% and about 80% of the fin height.

17. The device of claim 14,
wherein the second epitaxial layer has a peak layer height measured from a top surface of the isolation feature,
wherein the first plurality of fins has a fin height measured from the top surface of the isolation feature,
wherein the fin height is greater than the peak layer height by a difference between about 1 nm and about 10 nm.

18. The device of claim 14,
wherein the first epitaxial layer includes silicon and an n-type dopant with a first dopant concentration,
wherein the second epitaxial layer includes silicon and the n-type dopant with a second dopant concentration greater than the first dopant concentration.

19. The device of claim 18,
wherein the third epitaxial layer includes silicon and the n-type dopant with a third dopant concentration greater than the second dopant concentration.

20. The device of claim 19,
wherein the n-type dopant comprises arsenide or phosphorous,
wherein the second dopant concentration is between about $3 \times 10^{21}$ atoms per $cm^3$ and about $4 \times 10^{21}$ atoms per $cm^3$,
wherein the third dopant concentration is between about $4 \times 10^{21}$ atoms per $cm^3$ and about $5 \times 10^{21}$ atoms per $cm^3$.

* * * * *